(12) United States Patent
Wünsch et al.

(10) Patent No.: US 6,353,070 B1
(45) Date of Patent: Mar. 5, 2002

(54) STAR POLYMERS AND PROCESS FOR PRODUCING THE SAME

(75) Inventors: Josef Wünsch, Schifferstadt; Michael Geprägs, Bobenheim-Roxheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/242,731

(22) PCT Filed: Aug. 13, 1997

(86) PCT No.: PCT/EP97/04432

§ 371 Date: Feb. 22, 1999

§ 102(e) Date: Feb. 22, 1999

(87) PCT Pub. No.: WO98/08881

PCT Pub. Date: May 3, 1998

(30) Foreign Application Priority Data

Aug. 26, 1996 (DE) .......................................... 196 34 375

(51) Int. Cl.[7] .............................................. C08F 212/04
(52) U.S. Cl. ........................ 526/347; 526/113; 526/114; 526/116; 526/118; 526/185; 526/239; 526/240; 526/241; 526/274; 526/279; 526/310; 526/335; 526/340; 526/347
(58) Field of Search ................................ 526/113, 114, 526/116, 118, 185, 239, 240, 241, 274, 279, 310, 335, 340, 347

(56) References Cited

U.S. PATENT DOCUMENTS

| 4,222,882 A | * | 9/1980 | Brulet et al. ............ 252/51.5 A |
| 4,794,096 A | | 12/1988 | Ewen |
| 5,210,143 A | | 5/1993 | Silver |
| 5,502,133 A | | 3/1996 | Ishihara |
| 5,506,319 A | | 4/1996 | Takizawa |
| 5,723,511 A | * | 3/1998 | Kazmaier et al. ............. 522/35 |

FOREIGN PATENT DOCUMENTS

| EP | 210 615 | 2/1987 |
| EP | 284 708 | 10/1988 |
| EP | 311 099 | 4/1989 |
| EP | 421 659 | 4/1991 |
| EP | 490 269 | 6/1992 |
| EP | 572 990 | 12/1993 |
| EP | 584 646 | 3/1994 |
| WO | 91/09882 | 7/1991 |
| WO | 93/03067 | 2/1993 |

OTHER PUBLICATIONS

Beinert et al., Makromol. Chem. (1980), 181(1), 59–65.*
Falbe, Rompp Chem. 9, Stuttgart 1992, 4304.
J. Chem. Soc. Perkin Trans 1 1990, 3362–3363.
Beilsteins Handbuch, 1992, 367,473,485.
J. Org. chem, 369 (1989) 359–370.
Chem. Abs. vol. 114, Mar. 18–Apr. 1, 1991.

* cited by examiner

Primary Examiner—Helen L. Pezzuto
(74) Attorney, Agent, or Firm—Keil & Weinkauf

(57) ABSTRACT

Star polymers obtainable by polymerization of vinylaromatic monomers with a branching monomer unit containing at least two vinylaromatic functional radicals in the presence of a catalyst obtainable from A) a transition-metal complex from sub-group II to VIII, B) a cation-forming agent and C), if desired, an aluminum compound.

22 Claims, No Drawings

STAR POLYMERS AND PROCESS FOR PRODUCING THE SAME

The present invention relates to star polymers obtainable by polymerization of vinylaromatic monomers with a branching monomer unit containing at least two vinylaromatic functional radicals in the presence of a catalyst obtainable from A) a transition-metal complex from subgroup II to VIII, B) a cation-forming agent and C), if desired, an aluminum compound.

The present invention furthermore relates to a process for the preparation of these star polymers and to their use for the production of fibers, films and moldings, in particular injection molding materials [sic], and the resultant fibers, films and moldings.

Owing to its crystallinity, syndiotactic polystyrene has a very high melting point of about 270° C., high rigidity, tensile strength and dimensional stability, a low dielectric constant and high chemicals resistance. The mechanical property profile is retained even at above the glass transition temperature. The preparation of syndiotactic polystyrene in the presence of metallocene catalyst systems is disclosed, for example, in EP-A-210 615.

The low toughness and poor solubility, even in chlorinated solvents, and the low compatibility in blends with thermoplastics, for example PS, PB, PMMA, PE, PP, EP, PA6, PA66, PET, PBT, ABS, ASA etc., are disadvantageous. Furthermore, crystallization of the syndiotactic polystyrene frequently occurs from a conversion of as low as around 10%.

EP-A-572 990 describes metallocene-catalyzed copolymers of styrene and ethylene which have improved compatibility and high elasticity. However, these copolymers do not have the high stereotacticity and therefore do not achieve the high-temperature properties of syndiotactic polystyrene.

Copolymers of styrene and divinylbenzene are described in EP-A-311 099 and EP-A-490 269. Under the reaction conditions, only one vinyl group of the divinylbenzene reacts. The remaining vinyl groups are used for grafting reactions or crosslinked by means of free radicals on conditioning at about 230° C., molecular weights of from 1,000,000 to 6,000,000 only being obtained after this crosslinking reaction.

Star polymers belong to the class of the branched polymers (Falbe, Römpp Chemie Lexikon, Georg Thieme Verlag, 9th Edition, Stuttgart 1992, page 4304). They are usually prepared by polymerization of monomers with polyfunctional initiators, polyaddition of, for example, epoxides onto polyhydric alcohols or coupling of pre-prepared polymers, for example Li polystyrene, onto a center, for example silicon tetrachloride.

It is an object of the present invention to provide star polymers made from vinylaromatic monomers, which polymers simultaneously have high molecular weight and low melt viscosities, and a high end-group functionality for graft reactions, crosslinking reactions and other polymer-analogous reactions. Furthermore, the star polymers should have an essentially syndiotactic structure, ie. have a syndiotacticity of greater than 30%, in particular greater than 60%.

We have found that this object is achieved by the star polymers defined at the outset containing the branching monomer units containing at least two vinylaromatic functional radicals.

These polymers have high molecular weights of from 500,000 to 10,000,000 at the same time as low melt viscosities of less than 500 ml/10 min at 290° C. and a weight of 10 kg, and have significantly greater end-group functionalities compared with syndiotactic styrene of comparable molecular weight. In general, the end-group functionality is greater than 0.5 mol %, particularly preferably greater than 0.8 mol %.

These properties can be modified within a broad range by means of the molar ratio between the vinylaromatic monomer and branching monomer units according to the invention. The molar ratio between vinylaromatic monomers and the branching monomer unit is generally from 10,000,000:1 to 10:1.

The novel star polymers have a syndiotacticity greater than 60%, in general greater than 90%.

The branching monomers can, according to the invention, be compounds of the formula I

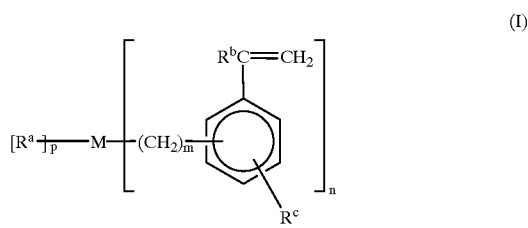

where $R^a$ is hydrogen, halogen or an inert organic radical having up to 20 carbon atoms, where, in a case where $p \geq 2$, the two radicals $R^a$ may be identical or different and can, together with the metal atom to which they are bonded, form a 3- to 8-membered ring, and $R^a$ may furthermore be a conventional complex ligand if M is a transition metal;

$R^b$ is hydrogen, $C_1$–$C_4$-alkyl or phenyl;

$R^c$ is hydrogen, $C_1$–$C_4$-alkyl, phenyl, chlorine or an unsaturated hydrocarbon radical having 2 to 6 carbon atoms;

M is C, Si, Ge, Sn, B, Al, Ga, N, P, Sb, Ti, Zr, Hf, V, Nb, Ta, Cr, Mo, W, Mn, Fe, Ru, Os, Co, Rh, Ir, Ni, Pd, Pt, Cu, Zn or Cd;

n is 2–6;

m is 0–20; and p is 0–4;

with the proviso that the sum n+p corresponds to the valence of M.

These monomers can be obtained, for example, via the Grignard compounds of chloro(alkyl)styrenes with the corresponding carbon, metal or transition-metal compounds, for example the halogen compounds. Such reactions have been described, for example, for the case where M is silicon, germanium or tin in K. Nakanishi, J. Chem. Soc. Perkin Trans. I, 1990, page 3362.

Particular preference is given to branching monomer units of the formula I in which M is carbon, silicon, germanium, tin or titanium, since they are readily accessible. The index m is preferably from 0 to 8, particularly preferably from 0 to 4.

The present invention also relates to the novel titanium-containing monomers of the formula Ia

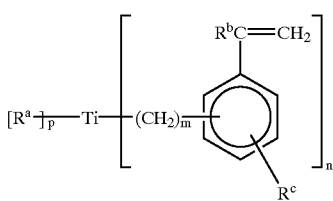

(Ia)

and in particular the titanium compound of the formula Ib

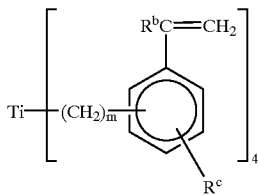

(Ib)

where $R^a$, $R^b$, $R^c$, m, n and p are as defined above.

The inert organic radicals $R^a$ are of no great significance for the process. Rather, they serve merely to saturate the free valences on M and can be selected in accordance with ready availability. For example, aliphatic, cycloaliphatic, aryl, heteroaryl or aralkyl radicals are suitable. Examples of aliphatic radicals are alkyl, alkoxy, alkenyl and alkynyl radicals having, for example, from 1 to 2 or 20 carbon atoms. Examples of cycloaliphatic radicals are cycloalkyl radicals having 3 to 8 carbon atoms. A methylene group in the alkyl or cycloalkyl radicals can also be replaced by an ether oxygen atom. Examples of aryl radicals are phenyl and naphthyl radicals, in which two phenyl groups can also be linked to one another via an oxygen atom. Examples of aralkyl radicals are those having 7 to 20 carbon atoms produced by combining a phenyl radical with an alkyl radical. Examples of heteroaryl radicals are pyridyl, pyrimidyl and furyl radicals. These radicals may also be further substituted, for example by alkyl, alkoxy, halogen, such as fluorine, chlorine or bromine, cyano, nitro, epoxy, carbonyl, ester groups, amides, etc. It is also possible for two of the radicals $R^a$, together with the atom M, to form a 3- to 6-membered ring, for example by two radicals $R^a$ forming an alkylene chain, in which one or more $CH_2$ groups may also be replaced by ether oxygen atoms.

If M is a transition metal, $R^a$ can also be a conventional σ- or π-bonded complex ligand, such as ethylene, allyl, butadiene, cyclopentadiene, mono- or polysubstituted cyclopentadienes, such as methylcyclopentadiene or pentamethylcyclopentadiene, benzene, cyclohexadiene, cycloheptatriene, cycloheptadiene, cyclooctatetraene, cyclooctatriene, cyclooctadiene, carbonyl, oxalato, cyano, isonitrile, fulminato-C, fulminato-O, cyanato, dinitrogen, ethyelenediamine, diethylenetriamine, triethylenetetramine, ethylenediamine tetraacetate, nitrosyl, nitro, isocyano, pyridine, α,α-dipyridyl, trifluorophosphine, phosphine, diphosphine, arsine or acetylacetonato.

$R^b$ is particularly preferably hydrogen or methyl. $R^c$ is hydrogen, $C_1$–$C_4$-alkyl, such as methyl, ethyl, propyl, isopropyl, n-butyl or butylisomers, phenyl, chlorine or an unsaturated hydrocarbon radical having 2 to 6 carbon atoms, such as vinyl, allyl, methallyl, butenyl or pentenyl.

Particularly suitable vinylaromatic compounds are those of the formula II

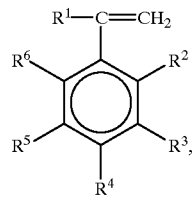

(II)

where
$R^1$ is hydrogen or $C_1$- to $C_4$-alkyl,
$R^2$ to $R^6$, independently of one another, are hydrogen, $C_1$- to $C_{12}$-alkyl, $C_6$- to $C_{18}$-aryl, or halogen, or two adjacent radicals together are a cyclic group having 4 to 15 carbon atoms.

Preference is given to vinylaromatic compounds of the formula II where
$R^1$ is hydrogen, and
$R^2$ to $R^6$ are hydrogen, $C_1$- to $C_4$-alkyl, chlorine or phenyl, or two adjacent radicals together are a cyclic group having 4 to 12 carbon atoms, so that compounds of the formula II are, for example, naphthalene derivatives or anthracene derivatives.

Examples of preferred compounds of this type are the following:
styrene, p-methylstyrene, p-chlorostyrene, 2,4-dimethylstyrene, 4-vinylbiphenyl, 2-vinylnaphthalene and 9-vinylanthracene.

It is also possible to use mixtures of different vinylaromatic compounds, where one component may also carry further hydrocarbon radicals, such as vinyl groups, allyl groups, methallyl groups, butenyl groups or pentenyl groups, preferably vinyl groups, on the phenyl ring. However, it is preferred to use only one vinylaromatic compound.

Particularly preferred vinylaromatic compounds are styrene and p-methylstyrene.

The preparation of vinylaromatic compounds of the formula II is known per se and is described, for example, in Beilstein 5, 367, 474, and 485.

The catalyst component A) used in accordance with the invention is a transition-metal complex from sub-group II to VIII, preferably from sub-group III to VIII. very particular preference is given to complexes of the metals titanium, zirconium and hafnium.

If the branching monomer unit of the formula I already contains a transition metal M, in particular titanium, it can, depending on the concentration used, also be used simultaneously as catalyst component A in addition to its function as branching unit.

The catalyst component A) is preferably a metallocene complex, particularly preferably of the formula III

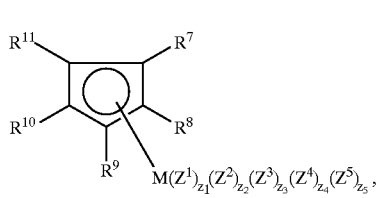

(III)

where
$R^7$ to $R^{11}$ are hydrogen, $C_1$- to $C_{10}$-alkyl, 5- to 7-membered cycloalkyl, which may itself carry $C_1$- to $C_6$-alkyl groups as substituents, $C_6$- to $C_{15}$-aryl or arylalkyl, it also being possible for two adjacent radicals together to form a cyclic group having 4 to 15 carbon atoms, or $Si(R^{12})_3$, where $R^{12}$ is $C_1$- to $C_{10}$-alkyl, $C_6$- to $C_{15}$-aryl or $C_3$- to $C_{10}$-cycloalkyl, M is a metal from sub-group III to VI of the Periodic Table of the Elements or a metal from the lanthanide series, $Z^1$ to $Z^5$ are hydrogen, halogen, $C_1$- to $C_{10}$-alkyl, $C_6$- to $C_{15}$-aryl, $C_1$- to $C_{10}$-alkoxy or $C_1$- to $C_{15}$-aryloxy, and $z_1$ to $z_5$ are 0, 1, 2, 3, 4 or 5, where the sum $z_1+z_2+z_3+z_4+z_5$ corresponds to the valence of M minus 1.

Particularly preferred metallocene complexes of the formula III are those in which M is a metal from sub-group IV of the Periodic Table of the Elements, ie. titanium, zirconium or hafnium, in particular titanium, and $Z^1$ to $Z^5$ are $C_1$- to $C_{10}$-alkyl, $C_1$- to $C_{10}$-alkoxy or halogen.

Examples of preferred metallocene complexes of this type are the following:

Pentamethylcyclopentadienyltitanium trichloride, pentamethylcyclopentadienyltrimethyltitanium and pentamethylcyclopentadienyltrimethoxytitanium.

It is also possible to use metallocene complexes as described in EP-A 584 646.

Mixtures of different metallocene complexes can also be used.

These complex compounds can be synthesized by methods known per se, preference being given to reaction of the appropriately substituted cyclic hydrocarbon anions with halides of titanium, zirconium, hafnium, vanadium, niobium or tantalum.

Examples of appropriate preparation processes are described, inter alia, in Journal of Organometallic Chemistry, 369 (1989), 359–370.

Suitable metallocenium ion-forming compounds B) in the catalyst system are open-chain or cyclic aluminoxane compounds, for example of the formula IV or V

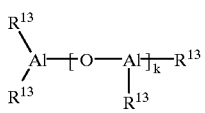

(IV)

or

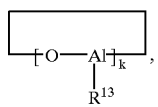

(V)

where $R^{13}$ is $C_1$- to $C_4$-alkyl, preferably methyl or ethyl, and k is an integer from 5 to 30, preferably from 10 to 25.

These oligomeric aluminoxane compounds are usually prepared by reacting a solution of trialkylaluminum with water, as described, inter alia, in EP-A 284 708 and U.S. Pat. No. 4,794,096.

In general, the oligomeric aluminoxane compounds are obtained as a mixture of both linear and cyclic chain molecules of various lengths, so that k can be regarded as a mean value. The aluminoxane compounds can also be in the form of a mixture with other alkyl metal compounds, preferably alkylaluminum compounds.

It has proven advantageous to use the metallocene complexes and the oligomeric aluminoxane compounds in such amounts that the atomic ratio between aluminum from the oligomeric aluminoxane compound and the transition metal from the metallocene complex is in the range from 10:1 to $10^6$:1, in particular in the range from 10:1 to $10^4$:1.

The metallocenium ion forming compound B) can also be a coordination complex compound taken from the group consisting of strong, neutral Lewis acids, ionic compounds with Lewis-acid cations and ionic compounds with Bronsted acids as cations.

The strong, neutral Lewis acids are preferably compounds of the formula VI $$M'X^1X^2X^3 \qquad (VI)$$

where $M^1$ is an element from main group III of the Periodic Table, in particular B, Al or Ga, preferably B, $X^1$, $X^2$ and $X^3$ are hydrogen, $C_1$- to $C_{10}$-alkyl, $C_6$- to $C_{15}$-aryl, alkylaryl, arylalkyl, haloalkyl or haloaryl, each having 1 to 10 carbon atoms in the alkyl radical and 6 to 20 carbon atoms in the aryl radical, or fluorine, chlorine, bromine or iodine, in particular haloaryls, preferably pentafluorophenyl.

Particular preference is given to compounds of the formula VI, in which $X^1$, $X^2$ and $X^3$ are identical, preferably tris(pentafluorophenyl)borane. These compounds and processes for their preparation are known per se and are described, for example, in WO 93/3067.

Suitable ionic compounds with Lewis-acid cations are compounds of the formula VII $$[(Y^{a+})Q_1Q_2\ldots Q_z]^{d+} \qquad (VII)$$

where

Y is an element from main group I to VI or sub-group I to VIII of the Periodic Table, $Q_1$ to $Q_z$ are radicals with a single negative charge, such as $C_1$- to $C_{28}$-alkyl, $C_6$- to $C_{15}$-aryl, alkylaryl, arylalkyl, haloalkyl, and haloaryl, each having 6 to 20 carbon atoms in the aryl radical and 1 to 28 carbon atoms in the alkyl radical, $C_1$- to $C_{10}$-cycloalkyl, which is unsubstituted or substituted by $C_1$- to $C_{10}$-alkyl, or are halogen, $C_1$- to $C_{28}$-alkoxy, $C_6$- to $C_{15}$-aryloxy, silyl- or mercaptyl groups, a is an integer from 1 to 6, z is an integer from 0 to 5, and d is the difference a–z, but where d is greater than or equal to 1.

Particularly suitable are carbonium cations, oxonium cations, sulfonium cations and cationic transition-metal complexes. Particular mention should be made of the triphenylmethyl cation, the silver cation and the 1,1'-dimethylferrocenyl cation.

They preferably have non-coordinating counterions, in particular boron compounds, as also mentioned in the WO 91/09882, preferably tetrakis(pentafluorophenyl) borate.

Ionic compounds with Brönsted acids as cations and preferably likewise non-coordinating counterions are mentioned in WO 93/3067; the preferred cation is N,N-dimethylanilinium.

It has proven particularly suitable if the molar ratio between boron from the metallocenium ion forming compound and transition metal from the metallocene complex is in the range from 0.1:1 to 10:1, in particular in the range from 1:1 to 5:1.

The catalyst system employed in the novel process can contain an aluminum compound as component C), for example of the formula VIII $$AlR^{14}R^{15}R^{16} \qquad (VIII),$$

where

R$^{14}$ to R$^{16}$ are hydrogen, fluorine, chlorine, bromine, iodine or C$_1$- to C$_{12}$-alkyl, preferably C$_1$- to C$_8$-alkyl.

The radicals R$^{14}$ and R$^{15}$ are preferably identical C$_1$–C$_6$-alkyl radicals, such as methyl, ethyl, isobutyl or n-hexyl; R$^{16}$ is preferably hydrogen.

Component C) is preferably present in the catalyst system in an amount from 1:2000 to 1:1, in particular from 1:800 to 1:10 (molar ratio between transition metal from III and Al from VIII).

The solvent used for the metallocene complex is usually an aromatic hydrocarbon, preferably having 6 to 20 carbon atoms, in particular xylene, toluene, ethylbenzene, or a mixture thereof.

The metallocene complexes may if desired be supported.

Examples of suitable support materials are silica gels, preferably those of the formula SiO$_2$.bAl$_2$O$_3$, in which b is a number in the range from 0 to 2, preferably from 0 to 0.5; ie. essentially aluminosilicates or silicon dioxide. The supports preferably have a particle diameter in the range from 1 to 200 μm, in particular from 30 to 80 μm. Such products are commercially available, for example as Silica Gel 332 from Grace.

Other supports include finely divided polyolefins, for example finely divided polypropylene or polyethylene, but also polyethylene glycol, polybutylene terephthalate, polyethylene terephthalate, polyvinyl alcohol, polystyrene, syndiotactic polystyrene, polybutadiene, polycarbonates or copolymers thereof.

The molar ratio between transition-metal catalyst A) and vinylaromatic monomer is generally from 1:1000 to 1:10,000,000, but preferably from 1:2000 to 1:1,000,000.

The present invention furthermore provides a process for the preparation of novel star polymers which can be carried out by observing the process conditions mentioned. A particular embodiment of the process comprises using a co-rotating, tightly meshing and thus self-cleaning twin-screw extruder, preferably in one step.

The reaction temperature is generally from –80 to 150° C., preferably from 0 to 120° C. However, it is also possible to apply a temperature gradient from 0 to 120° C. to the reaction tube via heatable jackets.

The extruder can consist of a plurality of individual zones which can be held at different temperatures.

The outer diameter of the corotating, preferably double-flighted compounding and conveying elements of the twin-screw extruder is preferably in the range from 25 to 70 mm, in particular from 30 to 58 mm.

The free space between the extruder barrel and the screw element is in the range from 0.2 to 0.8 mm, in particular from 0.3 to 0.5 mm.

The screw speed can be in the range from 3 to 500 revolutions per minute, preferably from 5 to 30 revolutions per minute.

The mean residence time in the extruder can be from 0.1 to 240 minutes, preferably from 2 to 20 minutes.

The mean residence time in the extruder can be regulated via the number of barrel blocks, which is preferably in the range from 6 to 20, in particular from 8 to 12, but particularly preferably 10, backventing taking place in the first block, the starting materials being metered into the second block, the reaction taking place in blocks 3 to 8, blocks 9 and 10 being heated to different temperatures if desired, and discharge taking place in block 10.

The process is preferably carried out in such a way that the vinylaromatic compound, the branching monomer unit, the metallocenium ion-forming compound B) and, if used, the aluminum compound C) are mixed under an inert-gas atmosphere and fed to the first extruder barrel block. In parallel, a solution or suspension of the transition-metal complex (A) can likewise be fed to the first block (zone).

Solvents and suspending media which may be mentioned are cyclic and acyclic hydrocarbons, such as butanes, pentanes, hexanes and heptanes, furthermore aromatic hydrocarbons, such as benzene, toluene and ethylbenzene, and oxygen-containing hydrocarbons, such as tetrahydrofuran, halogen-containing hydrocarbons, such as dichloromethane, and nitrogen-containing hydrocarbons, such as N-methylpiperidine, and mixtures thereof.

The amount metered in is preferably selected so that from 500 to 2000 g/h of the mixture of vinylaromatic compound, component B) and, if used, component C) are fed in along with from 100 to 200 cm$^3$/h of the solution or suspension of the metal complex.

The polymerization is preferably carried out in the vinylaromatic compound as reaction medium, ie. in bulk.

The process is technically simple to carry out, high conversions are achieved, and the risk of sticking or blockage of the extruder outlet apertures is low.

A further preferred embodiment comprises activating the reaction mixture of the vinylaromatic monomers, the branching monomer unit and the catalyst system consisting of A) a transition-metal complex from sub-group II to VIII, B) a cation-forming agent and C), if desired, an aluminum compound, by premixing and subsequently polymerizing the mixture in a mixer/compounder.

The premixing is preferably carried out at a temperature at which the reaction mixture is still liquid and the polymerization does not commence. Depending on the components used for the reaction mixture, this temperature is in the range from –30 to +140° C., preferably from 0 to 70° C., particularly preferably from 15 to 30° C. Furthermore, in the case of the novel activation, the premixing should preferably be carried out in such a way that the residence time and temperature are selected so that there is no damage to the catalyst, in spite of mixing sufficient for activation, and the polymerization reaction does not commence.

The activation by premixing the reaction mixture is advantageously carried out shortly or immediately before the polymerization reaction. The time between activation by premixing and polymerization is from 0 to 60 minutes, especially from 0.01 to 45 minutes, and particularly preferably from 0.1 to 30 minutes, it being preferred for the premixing to be carried out essentially without a reaction commencing.

The process is advantageously carried out without a solvent. In a particularly preferred embodiment of the process, the monomers employed initially act as solvent. In addition, it is advantageous to carry out the process in an inert-gas atmosphere, for example comprising nitrogen or argon, if possible with exclusion of moisture. It is also possible to meter hydrogen into the inert-gas stream.

The premixing is preferably carried out in such a way that no reaction takes place. It is furthermore advantageous that polymers are obtained in such a way that they can be processed further, preferably extruded, essentially immediately after the polymerization. This is preferably the case if the polymerization process is carried out to high yields and the polymer accordingly has a low residual monomer content of below 10% by weight, preferably below 5% by weight, particularly preferably below 3% by weight, based on the weight of the polymer. The residual monomer content remaining in the polymer can be removed, for example, by evaporation or by applying a vacuum. The novel process is preferably carried out in a mixing/compounding reactor with a downstream extruder without further work-up steps, for example removal of relatively large amounts of monomer, which are produced, in particular, at low conversions, by distillation, being necessary. The process thus permits further processing of the polymer essentially immediately after its preparation.

The resultant star polymers having syndiotactic chain branches and high molecular weights in combination with low melt viscosity are suitable for the production of fibers, for example monofilaments, films and moldings, in particular injection molding materials [sic] for electrical or high-temperature-resistant applications. Owing to their high olefinic end group content, they can also be modified by grafting, crosslinking or other polymer-analogous reactions and can be processed alone or in blends with thermoplastic polymers, rubbers, fillers, etc.

EXAMPLES

Examples 1–8 below illustrate the invention. Their properties are shown in Table 1 in comparison with syndiotactic polystyrene C1.

Tetrakis(4-vinylbenzyl)silane and tetrakis(4-vinylbenzyl) titanium were obtained by Grignard linking of 4-chloromethylstyrene to silicon tetrachloride or to titanium tetrachloride respectively.

The molar masses and molar mass distribution were determined by high-temperature GPC at 140° C. with 1,2, 4-trichlorobenzene as solvent. The calibration was carried out using polystyrene standards with a narrow molar mass distribution.

The melt viscosity index (MVI) was determined in accordance with DIN 53 735 at 290° C., and a weight of 10 kg.

The olefinic end groups were determined by $^{13}$C-NMR-spectroscopy.

Example 1

3.92 ml (6 mmol) of a solution of methylaluminoxane (MAO) in toluene (1.53 M) from Witco and 0.5 ml (0.5 mmol) of a solution of diisobutylaluminum hydride (DIBAH) in cyclohexane (1 M) from Aldrich were added to 208.3 g (2.0 mol) of styrene and $5.1 \times 10^{-5}$ g ($2.0 \times 10^{-7}$ mol) of tetrakis(4-vinylbenzyl)silane in a round-bottomed flask under a nitrogen blanket, and the mixture was heated to 60° C. 4.56 mg ($2 \times 10^{-5}$ mol) of pentamethylcyclopentadienyl-trimethyl titanium Cp*Ti(CH$_3$)$_3$ were then added for initiation, and the mixture was polymerized at 60° C. for 2 hours. The polymerization was terminated by addition of ethanol, and the polymer was washed with NaOH/ethanol and dried at 50° C. under reduced pressure.

Examples 2 to 7

Example 1 was repeated with increased proportions of tetrakis(4-vinylbenzyl)silane and the styrene/tetrakis(4-vinylbenzyl)silane ratios from Table 1.

Comparative Example C1

Example 1 was repeated without tetrakis(4-vinylbenzyl) silane.

Example 8

3.92 ml (6 mmol) of a solution of methylaluminoxane (MAO) in toluene (1.53 M) from Witco and 0.5 ml (0.5 mmol) of a solution of diisobutylaluminum hydride (DIBAH) in cyclohexane (1 M) from Aldrich were added to 208.3 g (2.0 mol) of styrene in a round-bottomed flask under a nitrogen blanket, and the mixture was heated to 60° C. 10.3 mg ($2 \times 10^{-5}$ mol) of tetrakis(4-vinylbenzyl)titanium were then added for initiation, and the mixture was polymerized at 60° C. for 2 hours. The polymerization was terminated by addition of ethanol, and the polymer was washed with NaOH/ethanol and dried at 50° C. under reduced pressure.

| Mw | 803,402 g/mol |
|---|---|
| Mw/Mn | 2.7 |
| MVI | 17.5 ml/10 min (290° C., 10 kg weight) |
| Olefinic end groups | 0.6 mol % |

TABLE 1

| Example | Styrene/tetrakis(4-vinylbenzyl)silane molar ratio | Mw[g/mol] | Mw/Mn | MVI [ml/10 min] | Olefinic end group conc. [mol-%] |
|---|---|---|---|---|---|
| C1 | — | 675 400 | 2.1 | 59.3 | 0.4 |
| 1 | 10$^7$/1 | 1 542 200 | 1.9 | 37.4 | 0.5 |
| 2 | 10$^6$/1 | 3 002 300 | 2.3 | 42.8 | 1.1 |
| 3 | 10$^5$/1 | 8 503 400 | 2.2 | 74.1 | 2.7 |
| 4 | 20 000/1 | n.b. | n.m. | 69.4 | 5.6 |
| 5 | 10 000/1 | n.m. | n.m. | 95.3 | 29.3 |
| 6 | 1000/1 | n.m. | n.m. | 124.2 | 63.3 |
| 7 | 100/1 | n.m. | n.m. | 170.2 | . . . | n.m.: not measurable

What is claimed is:

1. A star polymer obtained by polymerizing vinylaromatic monomers and a branching monomer unit containing at least two vinylaromatic functional radicals in the presence of a catalyst comprising
   A) a transition-metal complex of a metal of subgroup II to VIII,
   B) a cation-forming agent, and, optionally,
   C) an aluminum compound.

2. The star polymer defined in claim 1, wherein the branching monomer unit is a compound of formula I

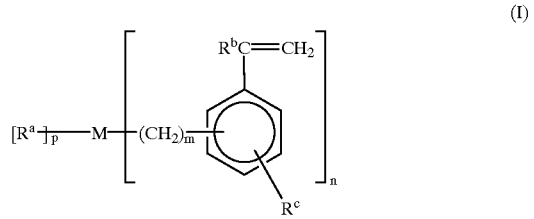

where
   R$^a$ is hydrogen, halogen or an inert organic radical having up to 20 carbon atoms, where, in a case where p≧2, the two radicals R$^a$ may be identical or different and can, together with the metal atom to which they are bonded, form a 3- to 8-membered ring, and R$^a$ may furthermore be a conventional complex ligand if M is a transition metal;
   R$^b$ is hydrogen, C$_1$–C$_4$-alkyl or phenyl;
   R$^c$ is hydrogen, C$_1$–C$_4$-alkyl, phenyl, chlorine or an unsaturated hydrocarbon radical having 2 to 6 carbon atoms;

M is C, Si, Ge, Sn, B, Al, Ga, N, P, Sb, Ti, Zr, Hf, V, Nb, Ta, Cr, Mo, W, Mn, Fe, Ru, Os, Co, Rh, Ir, Ni, Pd, Pt, Cu, Zn or Cd;

n is 2–6;

m is 0–20; and p is 0–4;

with the proviso that the sum of n+p corresponds to the valence of M.

3. The star polymer defined in claim 2, where M is carbon, silicon, germanium, tin or titanium.

4. The star polymer defined in claim 1, wherein the molar ratio between the vinylaromatic monomers and the branching monomer unit is from 10,000,000:1 to 10:1.

5. The star polymer defined in claim 1, where the vinylaromatic monomer is styrene or a styrene derivative.

6. The star polymer defined in claim 1 having an essentially syndioatactic structure.

7. A fiber, film or molding obtainable from the star polymer defined in claim 1.

8. The star polymer defined in claim 1, wherein the branching monomer unit is a titanium compound of formula Ia

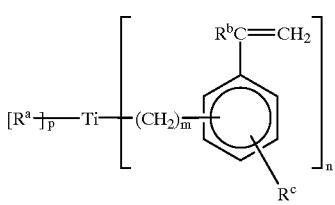

(Ia)

wherein $R^a$ is hydrogen, halogen or an inert organic radical having up to 20 carbon atoms, where, in a case where $p \geq 2$, the two radicals $R^a$ are identical or different and can, together with the metal atom to which they are bonded, form a 3- to 8-membered ring, and $R^a$ may furthermore be a conventional complex ligand;

$R^b$ is hydrogen, $C_1$–$C_4$-alkyl or phenyl;

$R^c$ is hydrogen, $C_1$–$C_4$-alkyl, phenyl, chlorine or an unsaturated hydrocarbon radical having 2 to 6 carbon atoms;

n is 2–4;

m is 0–20; and p is 0–2;

with the proviso that the sum of n+p corresponds to the valence of Ti.

9. The star polymer defined in claim 1, wherein the branching monomer unit is a titanium compound of formula Ib

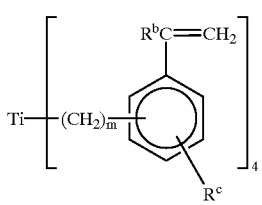

(Ib)

wherein $R^b$ is hydrogen, $C_1$–$C_4$-alkyl or phenyl;

$R^c$ is hydrogen, $C_1$–$C_4$-alkyl, phenyl, chlorine or an unsaturated hydrocarbon radical having 2 to 6 carbon atoms; and m is 0–20.

10. The star polymer defined in claim 1, wherein the metal of component A) is a transition metal of sub-groups III to VIII.

11. The star polymer defined in claim 1, wherein the metal of component A) is titanium, zirconium or hafnium.

12. The star polymer defined in claim 1, wherein component A) is a metallocene complex.

13. The star polymer defined in claim 12, wherein the metallocene complex is of formula III

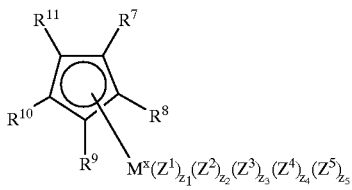

(III)

wherein $R^7$ to $R^{11}$ are each, independently from one another, hydrogen, $C_1$–$C_{10}$-alkyl, 5- to 7-membered cycloalkyl which is optionally substituted by $C_1$–$C_6$-alkyl, $C_6$–$C_{15}$-aryl or arylalkyl, or $Si(R^{12})_3$, or two radicals $R^7$ to $R^{11}$ which are bonded to adjacent ring atoms together form a cyclic group having 4 to 15 carbon atoms;

$R^{12}$ is $C_1$–$C_{10}$-alkyl, $C_6$–$C_{15}$-aryl or $C_3$–$C_{10}$-cycloalkyl;

$M^x$ is a metal of subgroup III to VI of the Periodic Table of the Elements, or is a metal from the lanthanide series;

$Z^1$ to $Z^5$ are each, independently from one another, hydrogen, halogen, $C_1$–$C_{10}$-alkyl, $C_6$–$C_{15}$-aryl, $C_1$–$C_{10}$-alkoxy or $C_6$–$C_{15}$-aryloxy; and $z_1$ to $z_5$ are each 0, 1, 2, 3, 4 or 5, and the sum of $z_1+z_2+z_3+z_4+z_5$ corresponds to the valence of $M^x$ minus 1.

14. The star polymer defined in claim 13, wherein $M^x$ is a metal of subgroup IV of the Periodic Table of the Elements, $Z^1$ to $Z^5$ are each, independently from one another, halogen, $C_1$–$C_{10}$-alkyl or $C_1$–$C_{10}$-alkoxy.

15. The star polymer defined in claim 13, wherein $M^x$ is titanium, zirconium or hafnium.

16. A process for producing a star polymer which comprises polymerizing vinylaromatic monomers and a branching monomer unit containing at least two vinylaromatic functional radicals in the presence of a catalyst comprising A) a transition-metal complex of a metal of subgroup II to VIII, B) a cation-forming agent and, optionally, C) an aluminum compound.

17. The process of claim 16, wherein the vinylaromatic monomer, the branching monomer unit and the catalyst system are premixed, and the reaction mixture is subsequently polymerized in a mixing/compounding reactor.

18. The process of claim 16, wherein the metal of component A) is a transition metal of sub-groups III to VIII.

19. The process of claim 16, wherein component A) is a metallocene complex.

20. The process of claim 19, wherein the metallocene complex is of formula III

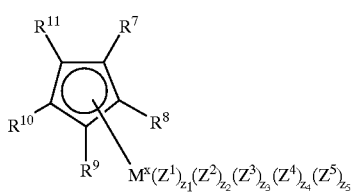

(III)

wherein $R^7$ to $R^{11}$ are each, independently from one another, hydrogen, $C_1$–$C_{10}$-alkyl, 5- to 7-membered cycloalkyl which is optionally substituted by $C_1$–$C_6$-alkyl, $C_6$–$C_{15}$-aryl or arylalkyl, or $Si(R^{12})_3$, or two radicals $R^7$ to $R^{11}$ which are bonded to adjacent ring atoms together form a cyclic group having 4 to 15 carbon atoms;

$R^{12}$ is $C_1$–$C_{10}$-alkyl, $C_6$–$C_{15}$-aryl or $C_3$–$C_{10}$-cycloalkyl;

$M^x$ is a metal of subgroup III to VI of the Periodic Table of the Elements, or is a metal from the lanthanide series;

$Z^1$ to $Z^5$ are each, independently from one another, hydrogen, halogen, $C_1$–$C_{10}$-alkyl, $C_6$–$C_{15}$-aryl, $C_1$–$C_{10}$-alkoxy or $C_6$–$C_{15}$-aryloxy; and $z_1$ to $z_5$ are each 0, 1, 2, 3, 4 or 5, and the sum of $z_1+z_2+z_3+z_4+z_5$ corresponds to the valence of $M^x$ minus 1.

21. The process of claim 20, wherein $M^x$ is a metal of subgroup IV of the Periodic Table of the Elements, $Z^1$ to $Z^5$ are each, independently from one another, halogen, $C_1$–$C_{10}$-alkyl or $C_1$–$C_{10}$-alkoxy.

22. The process of claim 20, wherein $M^x$ is titanium, zirconium or hafnium.

\* \* \* \* \*